United States Patent [19]

Gustowski et al.

[11] 4,156,721

[45] May 29, 1979

[54] METHOD OF PRODUCTION OF ACTIVE SUBSTANCE OF AN ANTINEPHROLITHIATIC, THE ANTINEPHROLITHIATIC, AND ITS APPLICATION FOR THERAPY OF THE NEPHROLITHIASIS

[75] Inventors: Włodzimierz Gustowski; Marian Kocòr, both of Warsaw, Poland; Chand K. Atal, RRL Jammu-Tawi, India; Alicja Orkiszewska, Piastów, Poland; Ryszard Olszewski, Pruszków, Poland; Tadeusz Wrociński, Poznań, Poland

[73] Assignee: Polska Akademia, Instytut Chemii Organicznej, Warsaw, Poland

[21] Appl. No.: 876,561

[22] Filed: Feb. 9, 1978

[30] Foreign Application Priority Data

Feb. 9, 1977 [PL] Poland .................................. 195886

[51] Int. Cl.² ............................................. A61K 35/78
[52] U.S. Cl. ...................................................... 424/195
[58] Field of Search ........................................... 424/195

[56] References Cited

FOREIGN PATENT DOCUMENTS 291710  2/1971  U.S.S.R.

OTHER PUBLICATIONS

Steimetz, "Codex Vegetabilis", (1957) RS51S8, entries 733 & 919.
The Dispensatory of the U.S.A., 24th Ed., (1947), J. B. Lippincott Co., Phila., Pa., p. 1389.

*Primary Examiner*—Donald B. Moyer
*Attorney, Agent, or Firm*—Haseltine, Lake & Waters

[57] ABSTRACT

A method of production of the active substance of an antilithiatic medicament, wherein ground seeds of the genus Dolichos are extracted with polar solvents, then the extract is contingently submitted to an acid hydrolysis, whereafter the acid hydrolyzate is contingently extracted with solvents immiscible with water, and then it is neutralized and contingently, is described.

The antilithiatic medicament contains the active substance produced according to the method of the invention. It is employed for therapy in nephrolithiasis.

15 Claims, No Drawings

METHOD OF PRODUCTION OF ACTIVE SUBSTANCE OF AN ANTINEPHROLITHIATIC, THE ANTINEPHROLITHIATIC, AND ITS APPLICATION FOR THERAPY OF THE NEPHROLITHIASIS

This invention concerns a method of production of the active substance of an antinephrolithiatic, the antinephrolithiatic per se, and its application in therapy for nephrolithiasis.

Urolithiasis belongs to one of the most frequently occurring diseases of the urinary system, and within certain populations it reaches 1–3.6%, wherein the formation of various concretions of calculi in the urinary system is not cleared hitherto. In relation to the etiology of said disease numerous hypotheses are set forth, but the low effectiveness of existing prophylactic treatments, and numerous drugs and methods used in the therapy thereof, among which even the surgical operations are used do not assure the desired effects.

The recurrences of lithiasis required as to search steadily for methods of non-operable treatment, that is for methods which will warrant the local dissolving of the calculi within the urinary tracts, which will be the simplest and most reliable method of removing them from the organism.

By local dissolving of the calculi in urinary tracts a direct application of chemical solvents to the calculus is to be understood.

Dissolving of the calculi in the urinary tracts is possible in two ways. The first thereof consists in the application of a solvent acting directly on the calculus, and being introduced, for instance, by means of a catheter. Said method is however accompanied with a hazard of numerous complications connected with mechanical damaging of the walls of urinary ducts, since instrumental manipulation is necessary. The other method consists in a change of the physical-and-chemical urinary medium, especially of the pH value of the urine, by oral or parenteral administration of suitable preparations.

The differentiated composition of the calculi makes necessary various preparations and different treatment methods to be employed. For instance, for dissolving the phosphatic calculi, a combined therapy is applied at present, consisting in the administration of agents acidifying the urine and forcing intensive diuresis, combined with strict diet and antibacterial preparations which are not always well tolerated by the patients. Among numerous agents acidifying the urine, administered locally by means of a catheter strong inorganic acids were tried, such as hydrochloric acid, nitric acid and aqua regia, these belonging to the best solvents of renal calculi. The effectiveness thereof depends, however, on the concentration. In solutions having concentrations below 0.01 n their activity decreases distinctly (see: — I. Sücker: Urologie, 3, 1964, p.218) and strong excitation of tissues by them makes impossible to employ the said acids over a longer period of time.

Introduction of citric acid by F. Albright, H. W. Sukowitch and R. Chute (Journal of the American Medical Association 113, 1939, p. 2049) was a significantly progressive step in investigations on dissolution of the calculi in urinary tracts. Citric acid is the basic component of solutions G and M proposed by H. J. Suby (Dissolution of urinary calculi, Journal of Urology 68, 1952, p.62). Solution G contains 32.25 g of citric acid, 3.84 g of magnesium oxide and 4.37 g of sodium carbonate in 1 l of water. Solution M differs from solution G by having higher content of sodium carbonate (8.84 g/l). As proved by the examinations in certain clinical cases, solutions G and M act only as inhibitors of the growth of urinary calculi. Also the known preparation Uralit U of Madaus, employed for dissolving the renal calculi, urinary calculi, and uric acid calculi contains citric acid, as it is composed of an hydrated complex of sodium and potassium salts of citric acid.

As effective for rapid dissolving of calculi, composed mainly of magnesium-ammonium phosphate, a preparation denominated "Renacidin" has been proved, it being a mixture of citric, glucuronic, maleic and benzene carboxylic acids, and of lactones, esters and salts of said acids. Renacidin is administered in a 10% solution. The complications, however, resulting in exiti, which many times occurred in the course of therapy with said preparation, had led to restrictions in the application thereof. In experiments in vivo it could be even stated an increase of the mass of the calculus treated with "Renacidin" in acidic environment.

As it results therefrom, the known antilithiatics contain mostly one compound or some compounds of chemical nature.

To known medicaments of plant origin employed for therapy of nephrolithiasis belongs Madaus's Uralit containing extracts of madder, horsetail, arnica and glycosides of convallaria and magnesium phosphate. The preparation is applied preventively in the case of assertion of oxalate calculi. A preparation of plant origin is also "Rubinex" containing dry extract of madder. The preparation is effective in cases of lithiasis of urinary organs, and especially in cases of lithiasis of ureters. It is, however, only limitedly applicable, being contraindicated as to diseases of liver and biliary tracts, as well as of intestine inflammation, and for patients with renal insufficiency.

The antilithiatic according to the present invention is a plant agent containing the extract of seeds of the genus Dolichos. The method of production of the active substance of the agent, also covered by the present invention, consists in that the ground seeds of Dolichos are extracted with polar solvents. The extraction is conducted within the temperature range of from room temperature up to the boiling point of the solvent.

As polar solvents, ethers are employed, for instance ethyl ether; esters, for instance ethyl acetate; ketones, for instance acetone; alcohols having 1 to 5 carbon atoms, or water, or mixtures thereof. The said organic solvents are employed preferably in a mixture with water in facultative proportion. This relates especially to the mixture of ethyl alcohol with water.

As the investigations have proved, the extract considerably inhibits the growth of renal calculi.

According to the present invention, the resulting extract can be further submitted to chemical processing in order to increase the activity of the active substance of the medicament. Thus, the resulting extract is submitted to acidic hydrolysis by means of aqueous solutions of a mineral or an organic acid, having a concentration of 0.5–25%, preferably 1–5%. As acids there may especially be employed sulphuric acid, hydrochloric acid, phosphoric acid, chloric acid, methanesulphonic or ethanesulphonic acid, chlorinated acetic acid, citric acid, lactic acid or their mixtures in facultative proportions.

The acidic hydrolysis of the extract is conducted at a temperature of from room temperature up to the boiling point of the reaction mixture, whereby, when the hydrolysis is conducted at room temperature, its duration is of 0.5-14 days, whereas at elevated temperatures the reaction time is shortened to 0.5-8 hours.

After completing the hydrolysis the precipitate is filtered or centrifuged and the acid hydrolyzate is either extracted with organic solvents, immiscible with water, such as ethyl ether, ethyl acetate, chloroform or higher alcohol, or it is directly neutralized to pH 4-8. The neutralization of the acid hydrolyzate is conducted with a concentrated solution of hydroxides or carbonates of alkali metals or alkaline earth metals or with ammonia, especially with sodium or potassium hydroxide or carbonate. A clear hydrolyzate is obtained, having a cherry-red-tea colour, which is contingently evaporated and, by means of known chemical agents, preserved against mould growth or bacteria.

The resulting active substance of the lithiatic according to the present invention is employed for treating nephrolithiasis, by itself, in form of an obtained solution, or it is processed into known forms of pharmaceutics such as tablets, dragees, powders, capsules, granules, syrups, elixirs, solutions, suspensions pastes and emulsions.

Said pharmaceutics can contain the active substance produced by the method according to the invention, alone or in combination with pharmacologically neutral and commonly used auxiliary substances and carriers, as for instance ascorbic acid, acetic acid, ethyl alcohol, glycerol, water, talc, lactose, saccharose, sorbitol, milk sugar, mannite, starch, corn starch, polyvinyl pyrrolidone, magnesium stearate, gelatine, cellulose derivatives, natural oils, waxes and the like. Furthermore, the preparations can also contain suitable preservatives, stabilizing agents, wetting agents, sweetening agents, taste agents, dyes, aromatic agents and the like.

The medicament according to the invention into the composition whereof the active substance produced in the method according to the invention enters, acts effectively, as it has been proved by pharmacological examinations, not only by inhibiting the growth of the renal calculi but also by dissolving them. That relates particularly to phosphate calculi, which constitutes over 60% of all calculi occuring in the human organism. That action manifests itself by administration to rats and mice, as experimental animals, in daily doses—in conversion to dry mass—of 0.01-0.5 g/kg of the body weight.

The antilithiatic according to the invention administered to rats in daily doses of 0.01 g, after 4-5 weeks of treatment causes a decrease of the phosphate-type calculus of human origin, introduced previously into the rat's bladder, down to 1/5 of its primary volume, and after 6 weeks it causes the complete dissolution thereof.

The pharmacological examinations on acute and protracted toxicity have proved that the antilithiatic according to the invention employed for therapy of the nephrolithiasis is a complete atoxic medicament. The dosis DL calculated after the Karber's method (L.Ther: Pharmakologische Methoden, Stuttgart, 1949) is 4 g/kg, converted to dry mass.

In examinations on the central nervous system, the medicament according to the invention demonstrates a tranquilizing action, reducing down to a half the cocaine irritation determined after the method of Modrakowski and Rusiecki (Bull. d.l.Acad.pol.d. Science et d.Lettre 42, 797, 1937).

Moreover, said medicament does not cause changes of the arterial blood pressure and of respiration rate of rats and cats, and does not influence the muscle strength and the equilibrium of mice. It demonstrates strong diuretic action, more than 3 times exceeding the standard, and saluretic action, and it also does not affect the amount of cholia.

The invention will now be explained in particular by means of examples which, however, do not limit the scope thereof.

A. Examples of production of the active substance of the antilithiatic according to the invention.

EXAMPLE 1

100 g of ground grains of the fodder beans Dolichos biflorus, screened through a screen with mesh of 0.65 mm, are submitted to an extraction with ethyl ether in a Soxhlet apparatus over 3 hours. The resulting ether extract is dried above magnesium sulphate and then evaporated until 2 g of product are obtained in oily yellow coloured form. The resulting extract is suspended in 100 g of distilled water, and in this form it is administered to rats having phosphate calculi of human origin in the bladder, introduced previously.

Strong action has been stated, inhibiting the growth of calculi in relation to the comparative group.

EXAMPLE 2

100 g of ground seeds of Dolichos are screened through a screen with mesh of 0.65 mm and submitted to an extraction by means of 1000 ml of mixture of a methyl alcohol with water in the proportion 1:1 by volume, at the boiling temperature of the mixture, for a period of 3 hours. The heating is then interrupted and the mixture is allowed to stand for 15 hours whereafter the extract is filtered and the alcohol is evaporated under a lowered pressure at a temperature of 50°-60° C., the remainder being then made up with water to the previous volume. The aqueous solution is then acidified with hydrochloric acid until a 3% solution is obtained. The mixture is then heated at 80° C. for 1 hour and allowed to cool down. The residue is filtered. A clear acid hydrolyzate is obtained, having cherry-red-tearosy colour and having a pH value of 1-1.2, said hydrolyzate being then neutralized to pH 5.5 by means of concentrated solution of sodium hydroxide. The resulting precipitate is filtered off and the clear solution is stabilized by adding 0.02 g of inhibitor. The hydrolyzate obtained in said way is then processed into the form of a pharmaceutic.

EXAMPLE 3

The process is conducted as defined in Example 2 with the difference that for extraction of the ground seeds the mixture of ethyl alcohol with water in a proportion of 1:1 is employed. The obtained hydrolyzate is evaporated to ¼ of its volume.

EXAMPLE 4

The process is conducted as defined in Example 2, but for extraction of the ground seeds 1000 ml of water are employed. The obtained hydrolyzate is evaporated to dry mass.

EXAMPLE 5

The process is conducted as defined in Example 2, but to the acid hydrolysis phosphoric acid is employed.

The obtained hydrolyzate is evaporated to ⅔ of its volume.

EXAMPLE 6

The process is conducted as defined in Example 4, but the obtained acid hydrolyzate is extracted with ether, then the etheric extract is processed as described in Example 1.

EXAMPLE 7

100 g of the ground seeds of Dolichos, screened through a screen with mesh 0.65 mm, are subjected to extraction by means of 500 ml of ethyl acetate at ambient temperature, for a period of 7 days. The resulting extract is processed as described in Example 1, or the ethyl acetate is evaporated under reduced pressure, the remainder being made up with water up to the previous volume. The aqueous solution is acidified with 25% citric acid until a 10% aqueous solution is obtained, and heated up to boiling, said temperature being maintained for 2 hours. After cooling the acid hydrolyzate down, 100 g of sugar and 0.2 g of anise oil are added, whereby the ready form of the pharmaceutic preparation is obtained, or the hydrolyzate is submitted to further processing. For this purpose the acid hydrolyzate is extracted with 500 ml of chloroform. After evaporating the chloroform the remainder is diluted with 300 ml of water and neutralized with a concentrated solution of potassium carbonate to the pH-value of 6. The resulting solution is then processed into a desired form of a pharmaceutic.

EXAMPLE 8

100 g of ground seeds of Dolichos are screened through a screen with mesh of 0.65 mm and submitted to extraction by means of 500 ml of a mixture of solvents (acetone - butyl alcohol) in a proportion by volume 1:4 at the ambient temperature. The obtained extract is filtered, and then the solvent is evaporated. The remainder is diluted with 500 ml of water, and processed into the desired form of a pharmaceutic, or the aqueous solution is acidified with 15 ml of a mixture of lactic acid and propionic acid in a proportion by volume of 60:40 and allowed to stand at the room temperature for a period of 13 days. The precipitated residue is filtered, and the acid hydrolyzate is extracted with ethyl acetate. The obtained extract is concentrated in vacuo to dryness, then diluted with 500 ml of water and alkalized by means of calcium hydroxide to the pH-value of 5.5. The precipitation is filtered off and the clear solution is stabilized with 0.15 g of the ester of hydroxybenzoic acid. The hydrolyzate obtained in this way is then processed into the desired form of a pharmaceutic.

EXAMPLE 9

The process is conducted as defined in Example 8 with the difference that the obtained acid hydrolyzate is neutralized with ammonium hydroxide.

B. Examples of preparations.

EXAMPLE 10

Solution.
Following components are mixed:

| | |
|---|---|
| Extract from Example 1 | 982.0 parts by weight |
| 30% sugar solution | 16.0 parts by weight |
| Mint oil | 0.5 parts by weight |
| Hydroxybenzoic ester | 15.0 parts by weight |
| Total | 1,013.5 parts by weight |

EXAMPLE 11

Suspension.

| | |
|---|---|
| Hydrolyzate from Example 2 | 982.0 parts by weight |
| Glycol | 4.8 parts by weight |
| Sodium salt of carboxymethylcellulose | 10.2 parts by weight |
| Mixture of essential oils | 0.5 parts by weight |
| Hydroxybenzoic ester | parts by weight |
| Total | 999.0 parts by weight |

EXAMPLE 12

Tablets.

| | |
|---|---|
| Dry hydrolyzate from Example 4 | 0.500 parts by weight |
| Magnesium stearate | 0.045 parts by weight |
| Ethylcellulose | 0.050 parts by weight |
| Talc | 0.015 parts by weight |
| Ethyl alcohol | 0.055 parts by weight |
| Water | 0.038 parts by weight |
| Total | 0.700 parts by weight |

The dry mass of the hydrolyzate is wetted with alcohol and intensively mixed with remaining components, whereafter the mixture is granulated by known methods.

The granulate is pressed in tablets in the weight of 0.7 g, each whereof contains 0.5 g of dry active substance of antilithiatic agent.

EXAMPLE 13

Paste.

| | | |
|---|---|---|
| Concentrated hydrolyzate from Example 5 | 600 | parts by weight |
| Gelatine | 1.8 | parts by weight |
| Agar-agar | 2.7 | parts by weight |
| Glycerin ointment prepared after the method described in FP III | 394.0 | parts by weight |
| Hydroxybenzoic ester | 1.5 | parts by weight |

The hydrolyzate is gelated by means of agar-agar with addition of glycerin and then mixed with the remaining components. Antilithiatic medicament is obtained in form of a paste appropriate for oral administration.

What is claimed is:

1. Method of production of active substance of an antilithiatic medicament, characterized in that ground seeds of the genus Dolichos are extracted with polar solvents, then the extract is contingently submitted to acid hydrolysis, whereafter the acid hydrolyzate is contingently extracted with solvents immiscible with water, and then it is neutralized and contingently concentrated.

2. Method as defined in claim 1, characterized in that ethers, esters, ketones, alcohols or water, or mixtures thereof are employed as polar solvents.

3. Method as defined in claim 2, characterized in that ethyl ether, ethyl acetate, acetone and alcohols having 1–5 carbon atoms are employed as polar solvents.

4. Methods as defined in claim 3, characterized in that polar organic solvents miscible with water are employed in a mixture with water in a facultative proportion.

5. Method as defined in claim 4, characterized in that a mixture of water with ethyl alcohol is employed.

6. Method as defined in claim 1, characterized in that the extraction of seeds is conducted within the temperature range of from room temperature to the boiling point of the solvent.

7. Method as defined in claim 1, characterized in that the acid hydrolysis of the extract is conducted with an organic or mineral acid having the concentration of 0.5–25%.

8. Method according to claim 7, wherein the organic or mineral acid is in the concentration of 1–5%.

9. Method as defined in claim 8, characterized in that sulphuric acid, hydrochloric acid, phosphoric acid, chloric acid, methane- or ethane-sulphonic acid, chlorinated acetic acid, citric acid, tartaric acid, propionic acid, lactic acid or mixtures thereof are employed.

10. Method as defined in claim 1, wherein the acid hydrolyzate is extracted with an organic solvent immiscible with water.

11. Method as defined in claim 10, wherein the extraction of the acid hydrolyzate is conducted by means of ethyl ether, ethyl acetate or a higher alcohol.

12. Method as defined in claim 1, characterized in that the hydrolysis is conducted with the temperature range from the room temperature to the boiling point of the reaction mixture, wherein the hydrolysis under the conditions of elevated temperature is conducted for 0.5–8 hours and the hydrolysis at the room temperature is conducted for 0.5–14 days.

13. Method as defined in claim 1, characterized in that the hydrolyzate is neutralized with a concentrated solution of sodium or potassium hydroxide or sodium or potassium carbonate or with ammonia.

14. A composition for the treatment of nephrolithiasis which comprises, as active ingredient, an antilithiatic agent prepared by the method of claim 1, and a pharmaceutically acceptable carrier.

15. A method of treating nephrolithiasis in patients by administering to said nephrolithiatic patients an antilithiatic amount of the composition as defined in claim 12.

* * * * *